United States Patent [19]
Antoci et al.

[11] Patent Number: 5,869,328
[45] Date of Patent: Feb. 9, 1999

[54] CUVETTE FOR PERFORMING A DIAGNOSTIC TEST ON A SPECIMEN

[75] Inventors: Frank Antoci, Stratford; James Hennessy, Trumbull, both of Conn.

[73] Assignee: CDC Technologies, Inc., Oxford, Conn.

[21] Appl. No.: 907,584

[22] Filed: Aug. 8, 1997

[51] Int. Cl.$^6$ .................................................... C12M 3/00
[52] U.S. Cl. ...................... 435/287.6; 422/61; 422/102; 356/246; 220/267; 220/278
[58] Field of Search .................. 422/61, 102; 435/287.6; 206/221; 215/DIG. 8, 253; 356/246; 220/266, 267, 277, 278

[56] References Cited

U.S. PATENT DOCUMENTS

| | | |
|---|---|---|
| 3,454,177 | 7/1969 | Bloom . |
| 3,582,283 | 6/1971 | Mirasol . |
| 4,076,592 | 2/1978 | Bradley ................................ 195/103.5 |
| 4,654,127 | 3/1987 | Baker et al. ............................ 204/1 T |
| 5,128,104 | 7/1992 | Murphy et al. .......................... 422/102 |

*Primary Examiner*—David A. Redding
*Attorney, Agent, or Firm*—Cummings & Lockwood

[57] ABSTRACT

In a cuvette for performing a diagnostic test on a specimen, a base defines a first chamber for receiving a reagent, and a second chamber for receiving a test specimen. The second chamber is defined by four side surfaces forming a rectangular configuration, and a base surface extending between the side surfaces. The base surface defines a frangible wall which is breakable in order to place the first chamber in fluid communication with the second chamber. A cover is coupled to the base and is moveable between an open position spaced away from the second chamber for permitting introduction of the specimen into the second chamber, and a closed position overlying and enclosing the second chamber. A self-aligning piercing member is provided on the cover and defines a tip engageable with the base surface of the second chamber upon movement of the cover into the closed position to thereby break the frangible wall, and in turn allow the test specimen to mix with the reagent in the second chamber. The piercing member also defines at least two alignment surfaces spaced inwardly from the tip and on opposite sides of the piercing member relative to each other. The alignment surfaces slidably contact the side walls of the second chamber upon movement of the cover to the closed position to thereby align the cover with the base.

21 Claims, 2 Drawing Sheets

CUVETTE FOR PERFORMING A DIAGNOSTIC TEST ON A SPECIMEN

FIELD OF THE INVENTION

The present invention relates generally to apparatus used in performing medical diagnostic tests, and more particularly to a cuvette for use in automated testing machines.

BACKGROUND OF THE INVENTION

The use of cuvettes or like receptacles in manual or automated medical diagnostic tests is well known. In a manual test, such as one which measures the amount of radiant energy absorbed by a test specimen, a technician dispenses precise quantities of a particular reagent and diluent into the cuvette. The contents are mixed and the amount of radiant energy absorbed by the mixture is measured. This provides the technician with an initial, baseline reading. Subsequently, the test specimen is introduced into the mixture and the test is conducted again. The results of the baseline test and the test incorporating the specimen are then compared and the amount of absorbed radiant energy attributable to the sample is determined. The accuracy of the test results is largely dependent on the precision with which the technician measures and dispenses the reagent and diluent into the cuvette.

To reduce the potential for human error, automated test equipment have employed cuvettes including one chamber wherein the reagent is prepackaged and another chamber for retaining the test specimen. The cuvettes also include a cover which is movable between an open position for accessing the chambers and a closed position overlying and enclosing the chambers. A post is provided on the cover for breaking a frangible surface in the chamber holding the specimen. During operation of the test equipment, the cover is moved from the open to the closed position causing the post to engage and break the frangible surface, and thereby allow the test specimen to mix with the reagent.

The automated test equipment often incorporates a carousel or like rotatably-driven carriage having individual receptacles for retaining a plurality of cuvettes. During a test, the carousel rotates each cuvette into a test position and a plunger or other device engages the cover of the cuvette, moving it from the open to the closed position. A difficulty sometimes occurs whereby the movement of the plunger causes the cover of the cuvette to be skewed relative to the chamber retaining the test specimen as the cover is moved from the open to the closed position. This in turn can cause the post to be forced against the edge of the chamber holding the test sample thereby preventing the cover from closing and the test specimen from mixing with the reagent.

Accordingly, it is an object of the present invention to provide a cuvette that overcomes the above-described drawbacks and disadvantages of the prior art.

SUMMARY OF THE INVENTION

The present invention is directed to a cuvette or like receptacle for performing a diagnostic test on a specimen, such as a blood sample for hematology and/or chemical analysis, wherein the cuvette includes a base defining a first chamber for receiving a reagent, and a second chamber spaced adjacent to the first chamber for receiving the specimen. The second chamber is defined by at least two side surfaces formed on opposite sides of the chamber relative to each other, and a base surface extending between the side surfaces. A portion of the base surface is defined by a frangible wall in order to permit the second chamber containing the specimen to be placed in fluid communication with the first chamber containing the reagent in order to mix the specimen and the reagent. A cover is coupled to the base and is moveable between an open position spaced away from the second chamber, and a closed position overlying and enclosing the second chamber.

An outwardly projecting piercing member or like protuberance is provided on the cover and defines a tip engageable with the base surface of the second chamber for breaking the frangible wall upon movement of the cover from the open into the closed position, and in turn placing the first chamber in fluid communication with the second chamber to thereby mix the specimen and reagent. The piercing member also includes at least two alignment surfaces that are spaced inwardly from the tip and on opposite sides of the piercing member relative to each other. The alignment surfaces are engageable with the opposing side surfaces of the second chamber upon movement of the cover into the closed position for aligning the cover with the base.

In a preferred embodiment of the present invention, the piercing member includes an intermediate tapered portion extending between the tip and the alignment surfaces and adapted to slidably contact an upper edge of the sides forming the second chamber to facilitate entry of the piercing member into the second chamber. The top of the piercing member also defines a tapered trailing edge adapted to slidably contact an upper edge of the sides forming the second chamber to further facilitate entry of the piercing member into the second chamber. In addition, the tip of the piercing member preferably defines a contoured surface adapted to be received within a mating surface defined by the base surface of the second chamber, to thereby further facilitate alignment of the cover with the base upon movement of the cover into the closed position.

Also in the preferred embodiment, the cuvette includes at least one locking tab projecting outwardly from at least one of the cover and the base. A corresponding recess is formed in at least one of the other of the cover and the base for receiving the locking tab upon movement of the cover into the closed position to fixedly secure the cover in place.

One advantage of the present invention is that the alignment surfaces of the piercing member cooperate with the corresponding surfaces of the second chamber to self-align the cover with the base upon movement of the cover into the closed position, and thereby prevent the cover from becoming skewed and the piercing member from becoming jammed against the walls of the second chamber, as may be encountered with use of the above-described prior art cuvettes.

BRIEF DESCRIPTION OF THE DRAWINGS

These and other features, aspects and advantages of the present invention will become clear with regard to the following description, appended claims, and accompanying drawings where:

DETAILED DESCRIPTION OF THE PREFERRED EMBODIMENT

Figure 1:
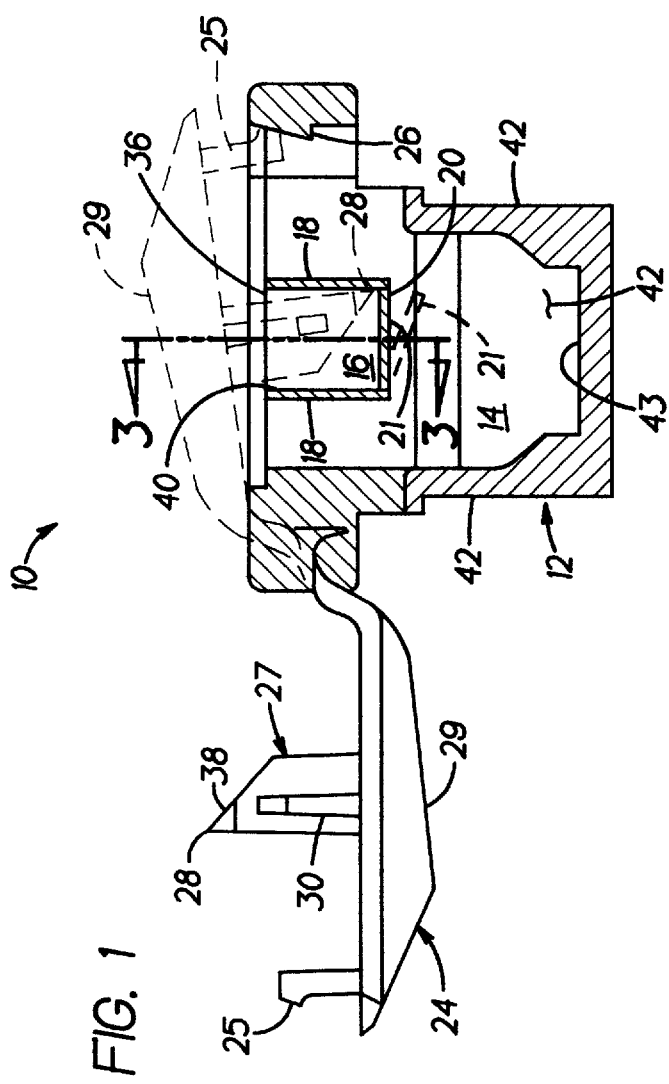
FIG. 1 is a partial cross-sectional, side elevational view of a cuvette embodying the present invention.

As shown in FIG. 1, a cuvette embodying the present invention for performing a diagnostic test on a specimen, such as a blood sample for hematology and/or chemistry analysis, is generally designated by the reference numeral 10. The cuvette 10 includes a base 12 defining a first chamber 14 for receiving a reagent, and a second chamber 16 for receiving a specimen. The second chamber 16 is defined by four side surfaces 18 forming a rectangular cross-sectional configuration, and a base surface 20 extending between the side surfaces. The base surface 20 is defined by a frangible wall 21 in order to permit the second chamber 16 containing the specimen to be placed in fluid communication with the first chamber 14 containing the reagent in order to mix the specimen and reagent.

A cover 24 is coupled to the base 12 and is movable between a first or open position spaced away from the second chamber 16 for permitting introduction of the specimen into the second chamber, and a second or closed position overlying and enclosing the second chamber. A locking tab 25 projects outwardly from the cover 24 and is adapted to be received in a corresponding recess 26 in the base 12 for locking the cover to the base with the cover in the closed position overlying and enclosing the second chamber 16.

In addition, a protuberance forming a self-aligning piercing member 27 projects outwardly from the cover 24 and defines a contoured tip 28 engageable with the base surface 20 of the second chamber 16 for piercing or breaking the frangible wall 21 upon movement of the cover from the open into the closed position, and in turn placing the first chamber 14 in fluid communication with the second chamber to thereby mix the specimen and the reagent.

Figure 2:
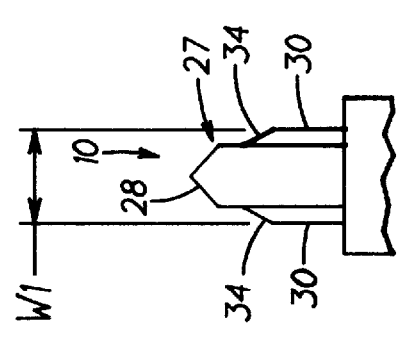
FIG. 2 is a partial, side elevational view of the piercing member and alignment surfaces of the cuvette of FIG. 1, taken from the left side.
Figure 3:
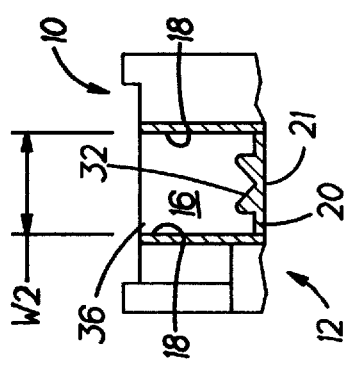
FIG. 3 is a partial cross-sectional view taken along line 3—3 of FIG. 1, and illustrating the second chamber in further detail.

As shown in FIG. 2, the piercing member 27 defines at least two alignment surfaces 30 spaced inwardly from the tip 28 and on opposite sides of the piercing member relative to each other. Referring to FIG. 1, the alignment surfaces 28 are dimensioned to be slidably received in contact with the opposing side surfaces 18 of the second chamber 16 upon movement of the cover 24 into the closed position for aligning the cover with the base 12 as the cover is moved from the open position to the closed position. Accordingly, as shown in FIG. 2, the alignment surfaces 30 define a width "W1" at the base of the piercing member 27, which, with reference to FIG. 3, is approximately equal to (but slightly less than) the width "W2" defined by the opposing side surfaces of the first chamber 16, in order to slidably receive the alignment surfaces in contact with, but without interfering with the side surfaces to thereby align the cover with the base. As also shown in FIG. 3, to further facilitate the alignment of the cover 24 with the base 12 the base surface 20 of the second chamber 16 defines a contoured surface 32 adapted to mate with the contoured surface of the tip 28, thereby causing the tip to seat in the base surface when the cover 24 is moved from the open position to the closed position overlying and enclosing the second chamber.

Referring back to FIG. 2, the piercing member 27 also includes an intermediate tapered portion 34 extending between the tip 28 and the alignment surfaces 30, and adapted to slidably contact an upper side edge 36 forming the second chamber 16 to facilitate entry of the piercing member into the second chamber as the cover is moved from the open to the closed position. In addition, the intermediate tapered surfaces 34 function to align the locking tab 25 with its recess 26 so that the tab is aligned with the recess upon receiving the intermediate tapered portion within the second chamber 16. The piercing member 27 also defines a sloped or tapered trailing edge 38 adapted to slidably contact an upper rear edge 40 forming the second chamber 16 to further facilitate entry of the piercing member into the second chamber. Note that the relative slopes of the surfaces of the tip 28, intermediate tapered portion 34, and alignment surfaces 30 are selected to minimize the overall length of the piercing member 27 while ensuring alignment of the locking tab 25 with its recess 26 upon movement of the cover 24 into the closed position.

As shown in FIG. 1, the base includes two pairs of opposing side surfaces 42, which in the preferred embodiment form a rectangular configuration. At least a portion of two of the side surfaces 42 positioned opposite relative to each other are transparent for optically testing a mixture in the first chamber 14. In addition, the base 12 includes a bottom surface 43 that is approximately parallel to the base surface 20 of the second chamber 16. While the base 12 has been described as having a rectangular configuration, the invention is not limited in this regard and other configurations, such as a round or oval configuration, may also be employed without departing from the broader aspects of the invention.

Figure 4:
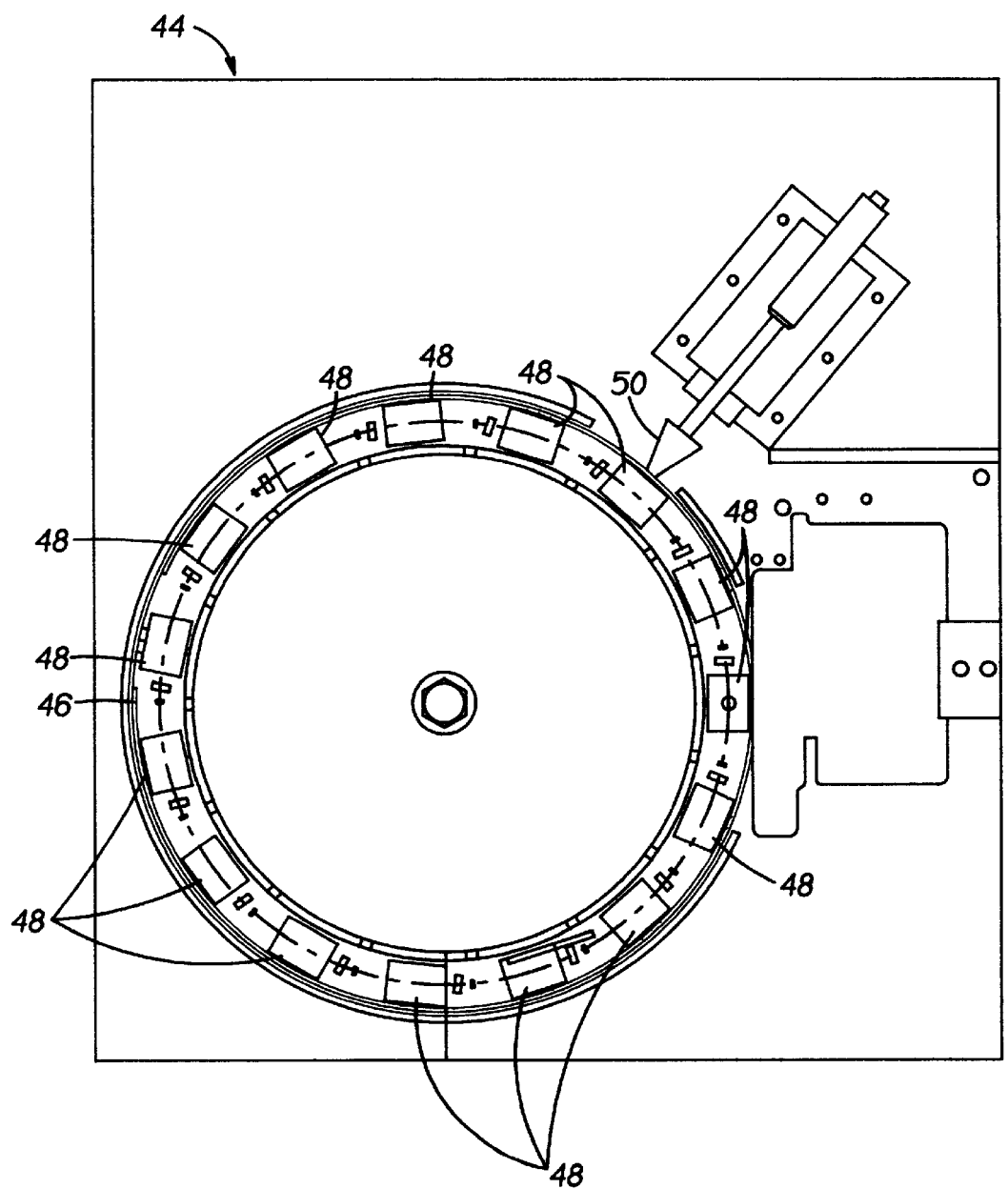
FIG. 4 is a plan view of a diagnostic test machine employing the cuvettes of the present invention.

Referring to FIG. 4, an automatic test machine for performing medical diagnostic tests is generally designated by the reference numeral 44 and includes a carousel or like rotatably driven carriage 46 having a plurality of recesses 48 for receiving a plurality of cuvettes 10. The first chamber 14 of each cuvette 10 is prefilled with a respective reagent as shown in FIG. 1, and a pipette or like device is employed to manually and/or automatically introduce the specimen into each second chamber 16. The cuvettes are then loaded into the recesses 48 with each cover 24 in the open position. Typically, the upper edge of each recess 48 (or surface adjacent thereto) engages the cover to in turn move the cover toward the closed position upon insertion of the cuvette into the recess. After an appropriate incubation period, the carousel is then rotatably driven to move each cuvette 10 into a respective test position. As the carousel 46 is rotated, a plunger 50 defining an approximately conical-shaped tip is actuated to engage with the tip the top surface 29 of each cuvette cover 24, and in turn move the cover into the fully-closed position with the locking tab 25 received within the recess 26 and the cover overlying and enclosing the first and second chambers, 12 and 16, respectively. As the cover 24 is moved into the closed position, the tip 28 of the piercing member 27 engages the base surface 20 of the second chamber 16, and in turn pierces the frangible wall 21 to thereby allow the test specimen to be mixed with the reagent in the first chamber 14.

While preferred embodiments have been shown and described, various modifications and substitutions may be made without departing from the spirit and scope of the invention. Accordingly, it is to be understood that the present invention has been described by way of example, and not by limitation.

What is claimed is:

1. A cuvette for performing a diagnostic test on a specimen, comprising:
   a base defining a first chamber for receiving a reagent, and a second chamber spaced adjacent to the first chamber for receiving the specimen, wherein the second chamber is defined by at least two side surfaces formed on opposite sides of the chamber relative to each other, and a base surface extending between the side surfaces, and at least a portion of the base surface is defined by a frangible portion for placing the first chamber in fluid communication with the second chamber;

a cover coupled to the base and movable between a first position spaced away from the second chamber for permitting introduction of the specimen into the second chamber, and a second position overlying and enclosing the second chamber;

a protuberance projecting outwardly from the cover and defining a tip engageable with the base surface of the second chamber upon movement of the cover into the second position for breaking the frangible portion and placing the first chamber in fluid communication with the second chamber, and at least two alignment surfaces spaced inwardly from the tip and on opposite sides of the protuberance relative to each other, and slidably contacting the side surfaces of the second chamber upon movement of the cover into the second position for aligning the cover with the base.

2. A cuvette for performing a diagnostic test on a specimen as defined by claim 1, wherein:

the second chamber includes an upper edge; and the protuberance includes an intermediate tapered portion extending between the tip and the alignment surfaces for slidably contacting the upper edge to facilitate entry of the protuberance into the second chamber.

3. A cuvette for performing a diagnostic test on a specimen as defined by claim 1, wherein the first chamber is defined by two pairs of opposing surfaces forming an approximately rectangular configuration.

4. A cuvette for performing a diagnostic test on a specimen as defined by claim 1, further comprising:

at least one locking tab projecting outwardly from at least one of the cover and the base; and wherein the other of the cover and the base defines a corresponding recess for receiving the locking tab upon movement of the cover into the second position to fixedly secure the cover to the base.

5. A cuvette for performing a diagnostic test on a specimen as defined by claim 1, wherein:

the second chamber includes an upper edge; and the protuberance defines a tapered trailing edge adapted to slidably contact the upper edge of the second chamber to facilitate entry of the protuberance into the second chamber.

6. A cuvette for performing a diagnostic test on a specimen as defined by claim 1, wherein the base surface of the second chamber defines a mating surface adapted to receive the tip of the protuberance to facilitate alignment of the cover with the base.

7. A cuvette for performing a diagnostic test on a specimen, comprising:

a base defining a first chamber for receiving a reagent, and a second chamber spaced adjacent to the first chamber for receiving the specimen, wherein the second chamber is defined by at least two side surfaces formed on opposite sides of the chamber relative to each other, and a base surface extending between the side surfaces, and at least a portion of the base surface is defined by a frangible portion for placing the first chamber in fluid communication with the second chamber;

a cover coupled to the base and movable between a first position spaced away from the second chamber for permitting introduction of the specimen into the second chamber, and a second position overlying the second chamber; and a protuberance extending from the cover, and including:

means for engaging and, in turn, breaking the frangible portion upon moving the cover in the direction from the first position to the second position, to thereby place the first chamber in fluid communication with the second chamber; and means for contacting at least two of the side surfaces of the second chamber upon moving the cover between the first and second positions and, in turn, aligning the cover with the base.

8. A cuvette for performing a diagnostic test on a specimen as defined by claim 7, wherein:

the means for engaging and, in turn, breaking the frangible portion includes a tip of the protuberance which is engageable with the base surface of the second chamber upon movement of the cover into the second position.

9. A cuvette for performing a diagnostic test on a specimen as defined by claim 7, wherein:

the means for contacting and, in turn, aligning the cover with the base includes at least two alignment surfaces spaced inwardly from a tip of the protuberance and on opposite sides of the protuberance relative to each other.

10. A cuvette for performing a diagnostic test on a specimen as defined by claim 9, wherein:

the second chamber includes an upper edge; and the protuberance includes an intermediate tapered portion extending between the tip and at least one of the alignment surfaces for slidably contacting the upper edge to facilitate entry of the protuberance into the second chamber.

11. A cuvette for performing a diagnostic test on a specimen as defined by claim 9, wherein:

the second chamber includes an upper edge; and the protuberance further defines a tapered trailing edge adapted to slidably contact the upper edge of the second chamber to facilitate entry of the protuberance into the second chamber.

12. A cuvette for performing a diagnostic test on a specimen as defined in claim 7, further comprising a reagent received within the first chamber.

13. A cuvette for performing a diagnostic test on a specimen as defined in claim 7, wherein the base is defined by at least one transparent portion for optically testing a specimen received in the first chamber.

14. A cuvette for performing a diagnostic test on a specimen as defined in claim 7, wherein the second chamber is defined by four side surfaces.

15. A cuvette for performing a diagnostic test on a specimen as defined in claim 14, wherein the four side surfaces form an approximately rectangular configuration.

16. A cuvette for performing a diagnostic test on a specimen, comprising:

a base defining a first chamber for receiving a reagent, and a second chamber spaced adjacent to the first chamber for receiving the specimen, wherein the second chamber is defined by a base surface, and at least one side wall extending along a periphery of the base surface, and wherein at least a portion of the base surface is defined by a frangible portion for placing the first chamber in fluid communication with the second chamber;

a cover coupled to the base and movable between a first position spaced away from the second chamber for permitting introduction of the specimen into the second chamber, and a second position overlying and enclosing the second chamber;

a protuberance extending from the cover and defining (i) a tip engageable with the base surface of the second chamber upon movement of the cover in the direction from the first position to the second position for breaking the frangible portion and, in turn, placing the first chamber in fluid communication with the second chamber, and (ii) at least two side surfaces for contacting the adjacent surfaces of the at least one side wall of the second chamber upon movement of the cover between the first and second positions to thereby align the cover with the base.

17. A cuvette for performing a diagnostic test on a specimen as defined in claim 16, wherein the at least two side surfaces of the protuberance are formed on approximately opposite sides of the protuberance relative to each other, and extend along a substantial portion of the protuberance in an axial direction thereof.

18. A cuvette for performing a diagnostic test on a specimen as defined in claim 16, wherein:

the second chamber is further defined by an upper edge; and the protuberance further defines at least one first tapered surface formed between the tip and at least one of the side surfaces of the protuberance for slidably contacting the upper edge of the second chamber to facilitate entry of the protuberance into the second chamber.

19. At least one cuvette as defined in claim 16, in combination with an apparatus for performing a diagnostic test on a specimen received within the at least one cuvette, wherein the apparatus for performing the diagnostic test comprises:

a support for supporting the at least one cuvette; and an actuator mounted adjacent to the support for contacting a side of the cover opposite the protuberance of the at least one cuvette, and in turn moving the cover and protuberance between the first and second positions.

20. At least one cuvette in combination with an apparatus for performing a diagnostic test on a specimen received within the at least one cuvette, as defined in claim 19, wherein at least one of the support and actuator is moveable relative to the other for moving the cover and protuberance between the first and second positions.

21. At least one cuvette in combination with an apparatus for performing a diagnostic test on a specimen received within the at least one cuvette, as defined in claim 20, wherein the support is rotatably mounted on the apparatus for rotatably moving the at least one cuvette relative to the actuator, and the actuator is movable between a (i) first position engageable with the cover for moving the cover between the first and second positions upon movement of the support, and (ii) a second position spaced away from the at least one cuvette for permitting movement of the support without engaging the cuvette with the actuator.

* * * * *